United States Patent [19]

Malhotra et al.

[11] Patent Number: 4,547,218

[45] Date of Patent: Oct. 15, 1985

[54] CERTAIN 3-NITRO-6-PHENOXY-2-PYRIDYL-OXY-PROPIONATES HAVING HERBICIDAL ACTIVITY

[75] Inventors: Sudarshan K. Malhotra, Walnut Creek; B. Clifford Gerwick, III, Concord, both of Calif.

[73] Assignee: The Dow Chemical Company, Midland, Mich.

[21] Appl. No.: 539,909

[22] Filed: Oct. 7, 1983

Related U.S. Application Data

[63] Continuation-in-part of Ser. No. 434,994, Oct. 18, 1982, abandoned.

[51] Int. Cl.[4] .................... C07D 213/64; A01N 43/40

[52] U.S. Cl. .................................. 71/94; 546/288; 546/296; 546/297; 546/194; 546/292

[58] Field of Search ............ 546/296, 297; 71/94

[56] References Cited

FOREIGN PATENT DOCUMENTS 0003295 11/1981 European Pat. Off. ............ 71/108
2906087 9/1980 Fed. Rep. of Germany .......... 71/94

Primary Examiner—Alan L. Rotman

[57] ABSTRACT

Novel compounds having a pyridinyl radical positioned adjacent to the propanoic acid portion, e.g., ethyl 2-((6-(2-chloro-4-(trifluoromethyl)-phenoxy)-3-nitro-2-pyridinyl)oxy)propionate, which are selective herbicides useful for controlling weeds in valuable crops.

6 Claims, No Drawings

CERTAIN 3-NITRO-6-PHENOXY-2-PYRIDYL-OXY-PROPIONATES HAVING HERBICIDAL ACTIVITY

CROSS REFERENCE TO RELATED APPLICATION

This application is a continuation-in-part of Ser. No. 434,994 filed Oct. 18, 1982, now abandoned.

BACKGROUND OF THE INVENTION

An active area of agricultural research is devoted to the production of more productive plant life, especially that plant life associated with food sources for man. One aspect of that research is the search for more efficient and more selective herbicides to control undesired vegetation in the presence of valuable crops, thereby reducing the competition for water, sunlight and nutrients and increasing yields.

DESCRIPTION OF THE PRIOR ART

European Pat. No. 003295 to Ciba Geigy and German Pat. No. 2,906,087 to Bayer disclose and claim a number of phenoxyphenoxy alkanoic acids and their derivatives as well as their use as selective herbicides and plant growth regulators.

SUMMARY OF THE INVENTION

The present invention is directed to novel compounds having herbicidal activity and which correspond to the formula

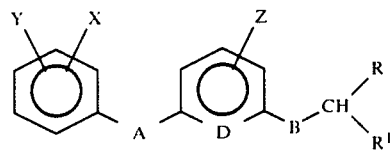
(I)

wherein A and B are independently O, S, NH or N-alkyl;

D is N, which may be ortho, meta or para to B;

R is H, halogen or lower alkyl;

$R^1$ is a monovalent organic radical which may contain N, O or S atoms; and

X, Y and Z are independently halogen, CN, $NO_2$, trifluoromethyl, hydrogen, lower alkyl, lower alkoxy, lower halogenated alkoxy, $CHCl_2$, $CCl_3$, $CHF_2$, $CCl_2F$, $CClF_2$; and their optically active isomers.

A variety of herbicidal compounds containing substituted pyridyl and phenoxy moieties joined via a bivalent —O— or —S— are described in the art. For example, U.S. Pat. Nos. 4,046,553; 4,317,913; 4,267,336; 4,213,774; 4,324,627, 4,309,547 and 4,325,729 and U.S. patent application Ser. Nos. 262,063 and 261,109, both filed July 30, 1980; Ser. No. 817,943, filed July 22, 1977 and Ser. No. 918,550, filed June 23, 1978, and European Patent Application 0004433 all describe such compounds and are incorporated herein by reference. In general, the moieties bonded to the pendant —O— group of the phenoxy in the herbicidal compounds described in these references will also be suitable as the monovalent organic radical represented by

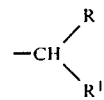

in the formula for the aforementioned novel compounds.

Advantageously, R is a $C_1$-$C_3$ alkyl group and $R^1$ is

wherein m is 1 or 2, n is an integer from 0 to 4 and $R^2$ is selected from moieties corresponding to one of the following formulae:

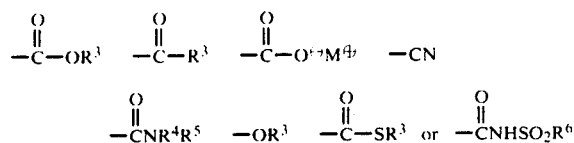

wherein $R^3$ is hydrogen or an aliphatic or alicyclic moiety, $R^4$ is hydrogen, an aliphatic or alicyclic moiety, or a moiety which in conjunction with $R^5$ forms a 5- or 6-member heterocyclic ring (e.g., —NR'R" is pyrrolidyl, piperidyl or morpholinyl group), $R^6$ is an alkyl or aryl moiety and $M^+$ is an alkali or alkaline earth metal or a lower ($C_1$-$C_6$) alkylsubstituted or unsubstituted ammonium moiety. $R^2$ is preferably a carboxylic acid group, an alkali or alkaline earth metal salt thereof, an amine salt thereof or a lower alkyl ester thereof, wherein "lower alkyl" includes straight, branched or cyclic alkyl groups containing no more than 6 carbon atoms. Preferably, n is the integer 0 or 2.

In the formula for the aforementioned novel compounds, X is preferably Cl or F, Y is preferably $CF_3$, A and B are preferably O, and D is ortho to A and B. Most preferred are the compounds in which R is $CH_3$ and $R^1$ is

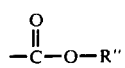

wherein R" is H, methyl, ethyl, isobutyl or n-butyl.

The compounds of formula (I) are useful both are pre- and postemergence herbicides. Preemergence herbicides are usually used to treat the soil in which a crop is to be planted, by application before or during seeding, or after seeding and before the crop emerges. Postemergence herbicides are applied after the crop plants have emerged from the soil. Compounds of formula (I) may be used as selective herbicides, preferably, preemergently, in a variety of crops including, for example, cotton, soya bean, peanuts, sugar beet, peas, wheat, barley and rice. They are preferably employed as preemergent selective herbicides in soybeans. They may also be used as total herbicides. They may be applied by any of the conventional techniques for applying herbicides. When applied as preemergence herbicides they may, for example, be sprayed on the surface of the soil before or during seeding, or after seeding and before emergence of the crop. In some situations, for example, in preemergence application to soya bean crops it may be advantageous to incorporate the compound of the invention into the soil before planting the crop. This may be done by applying the compound to the surface of the soil and then discing or harrowing the soil to mix the compound with the soil. Alternatively, use may be made of the applicators which have been developed for placing herbicides in a band beneath the surface of the soil.

The compounds of formula (I) may be combined with selective herbicides to achieve broadspectrum weed control in crops, for example, crops of soybean, cotton and peas. Alternatively, the second herbicide component may be a nonselective herbicide chosen to enhance the power of the compound of formula I as a total herbicide.

Examples of herbicides for use in admixture with compounds of formula (I) include, but are not restricted to, the following:

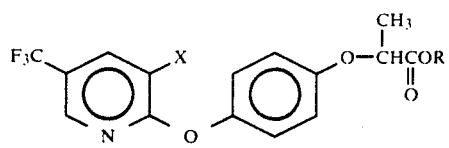

where X=H, Cl or F, and R=acid derivatives such as salts, esters, amides and the like.

The compounds employed in the method of the present invention are novel compounds and may be prepared using the requisite starting materials by the following illustrative methods.

EXAMPLE 1

Preparation of ethyl 2-(6-chloro-3-nitro-2-pyridinyl)oxypropanoate

A mixture of 8.8 grams of 3-nitro-6-chloro-2-pyridinol, 9 grams of ethyl α-bromopropionate and 6 grams of potassium carbonate was stirred in 50 ml of DMSO (dimethylsulfoxide) at ambient temperature for approximately 48 hours.

The reaction mixture was diluted with water and extracted with 1,1,1-trichloroethane. The extract was washed with water, dried and concentrated to a brown oil which was distilled via Kugelrohr affording a yellow liquid, b.p. 135°–140° C./2 mm pressure absolute. The liquid solidified on standing. The solid was recrystallized from hexane affording 5 grams of a yellow solid, m.p. 52°–55° C. It was shown to be the desired product by NMR (Nuclear Magnetic Resonance).

| Analysis: ($C_{10}H_{11}ClN_2O_5$) | | |
|---|---|---|
| | C | H | N |
| Calcd: | 43.72 | 4.01 | 10.2 |
| Found: | 43.29 | 3.95 | 10.11 |

EXAMPLE 2

Preparation of ethyl 2-((6-(2-chloro-4-(trifluoromethyl)phenoxy)-3-nitro-2-pyridinyl)oxy)propionate A mixture of the sodium salt of 2-chloro-4-(trifluoromethyl)phenol, which was prepared from 2.5 grams (14 millimoles) of the phenol and 0.75 gram of 50 percent NaH dispersed in paraffin, and 3.5 grams (12.75 millimoles) of ethyl 2-(6-chloro-3-nitro-2-pyridinyl)-oxypropionate in 50 ml of DMSO was stirred at room temperature for two hours. Water was added and the resulting mixture extracted with 1,1,1-trichloroethane. The extract was washed with water, dried over anhydrous $MgSO_4$ and concentrated under vacuo to give a yellow oil which solidified on trituration with hexane. The liquid was removed by filtration giving 2.1 g of white crystalline solid, m.p. 79°–81° C., which was characterized as the desired product by NMR (Nuclear Magnetic Resonance) and IR (infra-red).

| Analysis: ($C_{17}H_{14}ClF_3N_2O_6$) | | |
|---|---|---|
| | C | H | N |
| Calcd: | 46.95 | 3.22 | 6.44 |
| Found: | 46.92 | 3.25 | 6.55 |

Employing the above procedures and methods analogous to those in the described prior art and utilizing the appropriate starting materials, the following compounds were prepared:

| R | $R^1$ | X | Y | Z | A & B | Physical Properties* |
|---|---|---|---|---|---|---|
| $CH_3$ | CONHφ | Cl | $CF_3$ | $NO_2$ | O | 117–119° C. |
| $CH_3$ | CONHφCl | Cl | $CF_3$ | $NO_2$ | O | 139–145° C. |
| $CH_3$ | CO—N(piperidinyl) | Cl | $CF_3$ | $NO_2$ | O | 131–132° C. |
| $CH_3$ | CO—N(Me)(phenyl) | Cl | $CF_3$ | $NO_2$ | O | 129–131° C. |
| $CH_3$ | $COO(CH_2)_2OCH_3$ | Cl | $CF_3$ | $NO_2$ | O | $n_D^{25}$ 1.5260 |
| $CH_3$ | $CO_2$ n-butyl | Cl | $CF_3$ | $NO_2$ | O | $n_D^{25}$ 1.5222 |
| $CH_3$ | COO-phenyl | Cl | $CF_3$ | $NO_2$ | O | 119–120° C. |
| $CH_3$ | CO n-hexyl | Cl | $CF_3$ | $NO_2$ | O | $n_D^{25}$ 1.5170 |
| $CH_3$ | COO-(4-Cl-phenyl) | Cl | $CF_3$ | $NO_2$ | O | 125–126° C. |
| $CH_3$ | $COOCH_2$-phenyl | Cl | $CF_3$ | $NO_2$ | O | $n_D^{25}$ 1.5598 |
| $CH_3$ | $CO_2Et$ | $NO_2$ | Cl | $NO_2$ | O | 117–119° C. |
| $CH_3$ | $CO_2Et$ | Cl | $NO_2$ | $NO_2$ | O | 91.5–94° C. |
| $CH_3$ | $CO_2Et$ | Cl | Cl | $NO_2$ | O | 84.5–89.5° C. |

*M.P. unless otherwise indicated.

Employing the above procedures and methods analogous to those in the described prior art and utilizing the appropriate starting materials, the following compounds may be prepared:

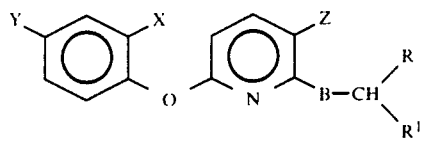

| | R | R¹ | X | Y | Z | B |
|---|---|---|---|---|---|---|
| 1 | H | CH₃ | Cl | CF₃ | NO₂ | O |
| 2 | H | CH₃ | F | CF₃ | NO₂ | O |
| 3 | H | CH₃ | Cl | Cl | NO₂ | O |
| 4 | H | CO₂H | Cl | CF₃ | NO₂ | O |
| 5 | H | CO₂H | F | CF₃ | NO₂ | O |
| 6 | CH₃ | CO₂H | Cl | CF₃ | NO₂ | O |
| 7 | CH₃ | CO₂CH₃ | F | CF₃ | NO₂ | O |
| 8 | CH₃ | CO₂Na | Cl | CF₃ | NO₂ | O |
| 9 | CH₃ | CO₂Et | Cl | CF₃ | Cl | O |
| 10 | CH₃ | CO₂Et | Cl | CF₃ | CN | O |
| 11 | CH₃ | OEt | F | CF₃ | NO₂ | O |
| 12 | CH₃ | OEt | Cl | CF₃ | Cl | O |
| 13 | F | F | Cl | CF₃ | NO₂ | O |
| 14 | F | CHF₂ | Cl | CF₃ | NO₂ | O |
| 15 | F | CHCl₂ | Cl | CF₃ | NO₂ | O |
| 16 | Cl | CHCl₂ | Cl | CF₃ | NO₂ | O |
| 17 | H | CN | Cl | CF₃ | NO₂ | O |
| 18 | CH₃ | CN | Cl | CF₃ | NO₂ | O |
| 19 | CH₃ | CONH₂ | Cl | CF₃ | NO₂ | O |
| 20 | CH₃ | CO₂iBu | F | CF₃ | CN | O |
| 21 | H | CH₃ | Cl | CF₃ | NO₂ | S |
| 22 | H | C₃H₇ | Cl | CF₃ | Cl | S |
| 23 | CH₃ | CO₂H | Cl | CF₃ | NO₂ | S |
| 24 | CH₃ | CO₂Na | Cl | CF₃ | NO₂ | S |
| 25 | CH₃ | CO₂Et | Cl | CF₃ | NO₂ | S |
| 26 | H | CO₂Me | Cl | CF₃ | NO₂ | S |
| 27 | H | CO₂Bu | Cl | Cl | CN | S |
| 28 | CH₃ | CH₂OMe | Cl | Cl | NO₂ | S |

The compounds utilized in the method of the present invention provide selective control of broad leaved weeds in valuable crops and give particular and advantageous selective postemergent control of such weeds.

For such uses, unmodified active ingredients of the present invention can be employed. However, the present invention embraces the use of the compounds in composition form with an inert material known in the art as an agricultural adjuvant or carrier in solid or liquid form. Thus, for example, an active ingredient can be dispersed on a finely-divided solid and employed therein as a dust or granule. Also, the active ingredients, as liquid concentrates or solid compositions comprising one or more of the active ingredients can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or water dispersions, with or without the addition of wetting, dispersing, or emulsifying agents. Suitable adjuvants of the foregoing type are well known to those skilled in the art.

The concentration of the active ingredients in solid or liquid compositions generally is from about 0.0003 to about 95 percent by weight or more. Concentrations from about 0.05 to about 50 percent by weight are often employed. In compositions to be employed as concentrates, the active ingredient can be present in a concentration from about 5 to about 98 weight percent. The active ingredient compositions can also contain other compatible additaments, for example, phytotoxicants, plant growth regulants and other biologically active compounds used in agriculture.

In further embodiments, the compounds of the present invention or compositions containing the same, can be advantageously employed in combination with one or more additional pesticidal compounds. Such additional pesticidal compounds may be insecticides, nematocides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in the ratio of from 1 to 100 parts of the compound of the present invention with from 100 to 1 parts of the additional compound(s).

The exact rate to be applied is dependent not only on a specific active ingredient being applied, but also on a particular action desired, the plant species to be modified and the stage of growth thereof as well as the part of the plant to be contacted with the toxic active ingredient. Thus, all of the active ingredients of the present invention and compositions containing the same may not be equally effective at similar concentrations or against the same plant species.

In selective postemergent operations a dosage of about 0.01 to about 20 pounds/acre (0.0112-2.24 kg/hectare) is generally applicable, although not all compounds are equally effective and some weeds are more difficult to control.

The following example illustrates the effects of the compounds of this invention.

EXAMPLE 3

In representative operations, each compound to be utilized in a series of tests is dissolved in acetone to one-half of the final volume (twice the final concentration) to be used and the acetone solution in each case is admixed with an equal volume of water containing 0.1 percent by weight of surface active material. The compositions, generally in the nature of an emulsion, were employed to spray separate respective plant species which had been grown to a 2-4 leaf stage in soil of good nutrient content in a greenhouse. Sufficient amounts were employed to provide various application rates as listed in the table. The various beds were positioned side by side and exposed to substantially identical conditions of temperature and light. Each bed was maintained so as to prevent any interaction with test compounds in different seed beds. Other plants were left untreated to serve as controls. After treatment, the plants were maintained for about two weeks under greenhouse conditions conducive for good plant growth and watered as necessary. The specific plant species, test compound and dosage and the percent postemergent control obtained are set forth in Table I below. Control refers to the reduction in growth compared to the observed results of the same untreated specie.

Plant species in these tests were:

| Common Name | Scientific Name |
|---|---|
| Soybeans | *Glycine max* |
| Morning Glory | *Ipomoea spp.* |
| Velvet Leaf | *Abutilon theophrasti* |
| Jimson Weed | *Datura stramonium* |

| -continued | |
|---|---|
| Common Name | Scientific Name |
| Pigweed | Amaranthus spp. |

TABLE I

POSTEMERGENT CONTROL OF PLANT SPECIES

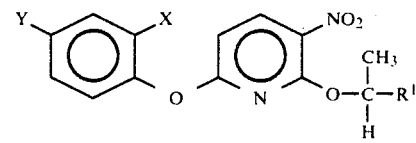

| Compound | | | | Percent Control At Indicated Application Rates (ppm) | | | | | |
|---|---|---|---|---|---|---|---|---|---|
| Y | X | $R^1$ | Plant Species | 500 | 250 | 125 | 62.5 | 31.25 | 15.6 |
| $CF_3$ | Cl | $CO_2C_2H_5$ | Soybeans | 50 | 50 | 60 | 50 | 30 | 20 |
| | | | Morning Glory | 100 | 100 | 100 | 99 | 80 | 25 |
| | | | Velvet Leaf | 100 | 100 | 100 | 100 | 100 | 100 |
| | | | Jimson Weed | 100 | 100 | 100 | 100 | 100 | 100 |
| | | | Pigweed | 100 | 100 | 100 | 100 | 100 | 100 |
| $CF_3$ | Cl | —CON(H)—C₆H₅ | Soybeans | NT | 20 | 15 | 10 | 0 | 0 |
| | | | Morning Glory | NT | 15 | 0 | 0 | 0 | 0 |
| | | | Velvet Leaf | NT | 0 | 0 | 0 | 0 | 0 |
| | | | Jimson Weed | NT | 10 | 0 | 0 | 0 | 0 |
| | | | Pigweed | NT | 90 | 80 | 40 | 0 | 0 |
| $CF_3$ | Cl | —CON(H)—C₆H₄—Cl | Soybeans | Inactive at 1000 ppm | | | | | |
| | | | Morning Glory | | | | | | |
| | | | Velvet Leaf | | | | | | |
| | | | Jimson Weed | | | | | | |
| | | | Pigweed | | | | | | |
| $CF_3$ | Cl | —CO—C₆H₅ | Soybeans | 60 | 50 | 45 | 35 | 40 | |
| | | | Morning Glory | 0 | 0 | 0 | 0 | 0 | |
| | | | Velvet Leaf | 90 | 80 | 70 | 50 | 35 | |
| | | | Jimson Weed | 30 | 15 | 10 | 5 | 0 | |
| | | | Pigweed | 90 | 80 | 70 | 50 | 35 | |
| $CF_3$ | Cl | —CON(CH₃)—C₆H₅ | Soybeans | 15 | 10 | 0 | 0 | 0 | |
| | | | Morning Glory | 0 | 0 | 0 | 0 | 0 | |
| | | | VelvetLeaf | 100 | 90 | 50 | 0 | 0 | |
| | | | Jimson Weed | 0 | 0 | 0 | 0 | 0 | |
| | | | Pigweed | 100 | 100 | 50 | 0 | 0 | |
| Cl | Cl | —$CO_2C_2H_5$ | Soybeans | 50 | 40 | 40 | 20 | 15 | 10 |
| | | | Morning Glory | 25 | 10 | 0 | 0 | 0 | 0 |
| | | | Velvet Leaf | 100 | 100 | 100 | 25 | 10 | 0 |
| | | | Jimson Weed | 100 | 100 | 100 | 60 | 40 | 20 |
| | | | Pigweed | 100 | 100 | 60 | 40 | 0 | 0 |
| $CF_3$ | Cl | —$CO_2C_6H_{13}$ | Soybeans | NT | 60 | 55 | 50 | 25 | 10 |
| | | | Morning Glory | NT | 60 | 40 | 40 | 0 | 0 |
| | | | Velvet Leaf | NT | 100 | 90 | 80 | 10 | 0 |
| | | | Jimson Weed | NT | 100 | 100 | 100 | 100 | 80 |
| | | | Pigweed | NT | 100 | 100 | 100 | 100 | 100 |
| $CF_3$ | Cl | —$CO_2C_2H_4OCH_3$ | Soybeans | NT | 90 | 60 | 50 | 40 | 30 |
| | | | Morning Glory | NT | 100 | 40 | 10 | 0 | 0 |
| | | | Velvet Leaf | NT | 100 | 95 | 60 | 30 | 0 |
| | | | Jimson Weed | NT | 100 | 100 | 100 | 100 | 100 |
| | | | Pigweed | NT | 100 | 100 | 100 | 100 | 100 |
| $CF_3$ | Cl | —$CO_2$ n-butyl | Soybeans | NT | 70 | 60 | 60 | 25 | 15 |
| | | | Morning Glory | NT | 50 | 10 | 0 | 0 | 0 |
| | | | Velvet Leaf | NT | 100 | 100 | 90 | 90 | 15 |
| | | | Jimson Weed | NT | 100 | 100 | 100 | 100 | 80 |
| | | | Pigweed | NT | 100 | 100 | 100 | 100 | 100 |
| $CF_3$ | Cl | —$CO_2$—C₆H₅ | Soybeans | NT | 65 | 55 | 40 | 30 | 20 |
| | | | Morning Glory | NT | 20 | 20 | 0 | 0 | 0 |
| | | | Velvet Leaf | NT | 100 | 90 | 90 | 50 | 20 |
| | | | Jimson Weed | NT | 100 | 100 | 100 | 100 | 50 |
| | | | Pigweed | NT | 100 | 100 | 100 | 90 | 80 |
| $CF_3$ | Cl | —$CO_2$—C₆H₄—Cl | Soybeans | 90 | 65 | 35 | 30 | 20 | 15 |
| | | | Morning Glory | 20 | 0 | 0 | 0 | 0 | 0 |
| | | | Velvet Leaf | 95 | 85 | 70 | 10 | 0 | 0 |
| | | | Jimson Weed | 100 | 90 | 70 | 70 | 50 | 15 |
| | | | Pigweed | 100 | 85 | 80 | 90 | 0 | 0 |

TABLE I-continued

POSTEMERGENT CONTROL OF PLANT SPECIES

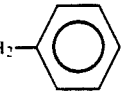

| Compound | | | | Percent Control At Indicated Application Rates (ppm) | | | | | |
|---|---|---|---|---|---|---|---|---|---|
| Y | X | R[1] | Plant Species | 500 | 250 | 125 | 62.5 | 31.25 | 15.6 |
| CF$_3$ | Cl | —CO$_2$CH$_2$— 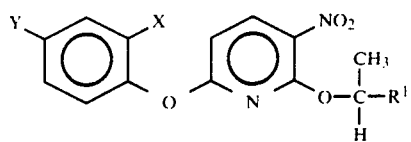 | Soybeans | 75 | 75 | 60 | 30 | 25 | 10 |
| | | | Morning Glory | 25 | 10 | 0 | 0 | 0 | 0 |
| | | | Velvet Leaf | 99 | 95 | 80 | 75 | 20 | 0 |
| | | | Jimson Weed | 95 | 100 | 100 | 90 | 20 | 20 |
| | | | Pigweed | 100 | 100 | 100 | 100 | 80 | 70 |

EXAMPLE 4

In a representative operation each compound to be utilized in a series of tests is dissolved in acetone to ½ the final volume to be used and the acetone solution in each case is then admixed with an equal volume of water containing 0.1 percent by weight of TWEEN ®20 surfactant, a commercially available product from Atlas Chemical Company. Each compound is an active compound of Formula I. The compositions, generally in the nature of an emulsion, are employed to treat separate respective seed beds of agricultural soil of good nutrient content wherein each seed bed contains separate groups of good, viable seeds. The various beds are positioned side by side and exposed to substantially identical conditions of temperature and light. Each bed is maintained so as to prevent any interaction with test compounds in different seed beds. Each seed bed is treated with one of the compositions as a spray applied uniformly throughout the surface of the bed using predetermined amounts of a given test compound. The compositions are applied so that respectively different seed beds are treated with one of each of the test compounds. Another seed bed is treated only with water to serve as a control. After treatment, the seed beds are maintained for three weeks under greenhouse conditions conducive for good plant growth and watered as necessary. The specific plant species, test compound and dosage and the percent control obtained are set forth in Table II below. Percent control refers to the reduction in growth compared to the observed results of the controls.

TABLE II

PREEMERGENT CONTROL OF PLANT SPECIES

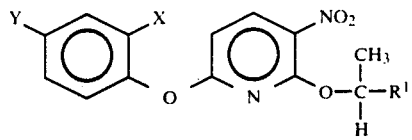

| Compound | | | | Percent Control At Indicated Application Rates (lbs/acre) | | | |
|---|---|---|---|---|---|---|---|
| Y | X | R[1] | Plant Species | 0.1 | 0.5 | 0.25 | 0.125 |
| CF$_3$ | Cl | CO$_2$C$_2$H$_5$ | Soybeans | 0 | 0 | 0 | 0 |
| | | | Velvet Leaf | 100 | 100 | 100 | 100 |
| | | | Jimson Weed | 100 | 100 | 100 | 100 |
| | | | Pigweed | 100 | 100 | 100 | 100 |
| | | | Yellow Foxtail | 100 | 100 | 30 | 10 |
| CF$_3$ | Cl | —CO$_2$C$_2$H$_5$ | Soybeans | 0 | 0 | 0 | 0 |
| | | | Velvet Leaf | 100 | 100 | 70 | 20 |
| | | | Jimson Weed | 100 | 30 | 10 | 0 |
| | | | Pigweed | 100 | 100 | 30 | 0 |
| CF$_3$ | Cl | —CO$_2$C$_6$H$_{13}$ | Soybeans | 0 | 0 | 0 | 0 |
| | | | Velvet Leaf | 90 | 30 | 0 | 0 |
| | | | Jimson Weed | 70 | 20 | 0 | 0 |
| | | | Pigweed | 90 | 30 | 0 | 0 |
| CF$_3$ | Cl | —CO$_2$(C$_2$H$_4$)OCH$_3$ | Soybeans | 20 | 0 | 0 | 0 |
| | | | Velvet Leaf | 90 | 30 | 0 | 0 |
| | | | Jimson Weed | 100 | 70 | 30 | 0 |
| | | | Pigweed | 100 | 100 | 100 | 80 |
| CF$_3$ | Cl | —CO$_2$ n-butyl | Soybeans | 0 | 0 | 0 | 0 |
| | | | Velvet Leaf | NT | NT | NT | NT |
| | | | Jimson Weed | 100 | 60 | 0 | 0 |
| | | | Pigweed | 100 | 100 | 90 | 30 |

TABLE II-continued
PREEMERGENT CONTROL OF PLANT SPECIES

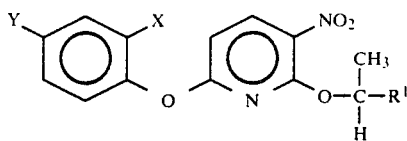

| Compound | | | | Percent Control At Indicated Application Rates (lbs/acre) | | | |
|---|---|---|---|---|---|---|---|
| Y | X | R¹ | Plant Species | 0.1 | 0.5 | 0.25 | 0.125 |
| $CF_3$ | Cl | —CO$_2$—⌬ | Soybeans | 0 | 0 | 0 | 0 |
| | | | Velvet Leaf | 90 | 30 | 0 | 0 |
| | | | Jimson Weed | 50 | 30 | 0 | 0 |
| | | | Pigweed | 30 | NT | 0 | 0 |

We claim:

1. A compound having the formula

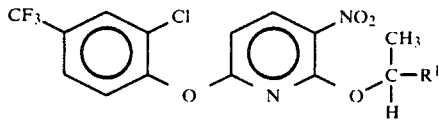

wherein $R^1$ is a carboxyl moiety, a $C_1-C_6$ alkyl ester thereof, an alkali or alkaline earth metal salt thereof, a $C_1-C_6$ alkyl substituted or unsubstituted ammonium salt thereof, or a benzyl or $C_3-C_6$ alkoxyalkyl ester thereof and their optically active isomers.

2. Compound of claim 1 wherein $R^1$ is $-COOC_2H_5$.

3. A composition comprising a herbicidally-effective amount of a compound having the formula

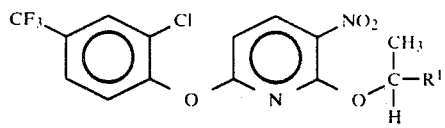

wherein $R^{1'}$ is a carboxyl moiety, a $C_1-C_6$ alkyl ester thereof, an alkali or alkaline earth metal salt thereof, a $C_1-C_6$ alkyl substituted or unsubstituted ammonium salt thereof, or a benzyl or $C_3-C_6$ alkoxyalkyl ester thereof and their optically active isomers.

4. Composition of claim 3 wherein $R^1$ is $-COOC_2H_5$.

5. The method of controlling undesired plant growth which comprises applying to the locus of said plants a herbicidally-effective amount of a compound having the formula

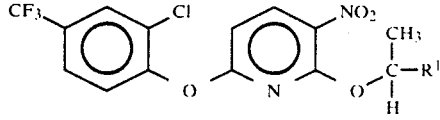

wherein $R^1$ is a carboxyl moiety, a $C_1-C_6$ alkyl ester thereof, an alkali or alkaline earth metal salt thereof, a $C_1-C_6$ alkyl substituted or unsubstituted ammonium salt thereof, or a benzyl or $C_3-C_6$ alkoxyalkyl ester thereof and their optically active isomers.

6. The method of claim 5 wherein $R^1$ is $-COOC_2H_5$.

* * * * *